United States Patent [19]

Drake

[11] 4,140,720

[45] Feb. 20, 1979

[54] COBALT HYDROGENATION CATALYST ACTIVATION

[75] Inventor: Charles A. Drake, Bartlesville, Okla.

[73] Assignee: Phillips Petroleum Company, Bartlesville, Okla.

[21] Appl. No.: 798,525

[22] Filed: May 19, 1977

[51] Int. Cl.$^2$ .................. C07C 85/12; B01J 23/40; B01J 23/74

[52] U.S. Cl. .................. 260/583 P; 252/447; 252/472; 260/570.9; 260/583 K; 260/584 R; 260/584 C; 260/690; 560/155; 562/575

[58] Field of Search .............. 260/578, 583 K, 583 P; 252/472

[56] References Cited

U.S. PATENT DOCUMENTS

| | | | |
|---|---|---|---|
| 1,151,003 | 8/1915 | Ellis | 252/472 |
| 2,165,515 | 7/1939 | Schmidt | 260/583 K |
| 2,436,368 | 2/1948 | Weber et al. | 260/583 K |
| 3,178,373 | 4/1965 | Groebe | 252/472 X |
| 3,223,735 | 12/1965 | Scholz et al. | 260/583 K |
| 3,255,248 | 6/1966 | Suessenguth et al. | 260/563 |
| 3,384,666 | 5/1968 | Lichtenwalter | 260/583 K |
| 3,427,356 | 2/1969 | Baer et al. | 260/583 K |
| 3,829,393 | 8/1974 | Sutherland et al. | 252/459 |
| 3,891,707 | 6/1975 | Waddan | 260/583 K |
| 3,972,938 | 8/1976 | Voges et al. | 260/583 K |

FOREIGN PATENT DOCUMENTS

| | | | |
|---|---|---|---|
| 55959 | 5/1967 | Fed. Rep. of Germany | 260/583 K |
| 42-9933 | 5/1967 | Japan | 260/583 K |
| 1342577 | 1/1974 | United Kingdom | 252/472 |
| 1419767 | 12/1975 | United Kingdom | 252/472 |

*Primary Examiner*—Winston A. Douglas
*Assistant Examiner*—John Doll

[57] ABSTRACT

A method for activating a cobalt hydrogenation catalyst in which the catalyst is contacted with a flow of hydrogen for a time sufficient for activation at an activation temperature below 250° C., and at an activation pressure above 1000 psig. The activated catalyst is used in hydrogenating a chemical compound containing at least one nitrile group to form an amine.

10 Claims, No Drawings

4,140,720

COBALT HYDROGENATION CATALYST ACTIVATION

BACKGROUND OF THE INVENTION

This invention relates to hydrogenation. In one of its aspects this invention relates to the activation of cobalt hydrogenation catalysts. In another one of its aspects this invention relates to the hydrogenation of nitriles to amines.

In one of its concepts this invention provides an improved hydrogenation catalyst for the hydrogenation of nitriles to amines.

The production of amines from nitriles has become important because of the use of certain amines as intermediates for the preparation of fiber grade polyamides and other polymeric materials. Hydrogenation of nitriles to produce amines is by no means new in the art. Methods by which the efficiency of the reaction can be improved have become of increasing importance. It has now, surprisingly, been discovered that the efficiency of hydrogenation of nitriles to produce amines can be improved by the manner in which cobalt catalysts, which are familiar catalysts for hydrogenation, are activated.

It is therefore an object of this invention to provide a method for activating cobalt hydrogenation catalysts. It is another object of this invention to provide a method for hydrogenating nitriles to produce amines using a cobalt hydrogenation catalyst activated by the disclosed method.

Other aspects, objects, and the various advantages of this invention will become apparent upon reading this specification and the appended claims.

STATEMENT OF THE INVENTION

According to the invention, a cobalt hydrogenation catalyst is activated by contacting the catalyst with a flow of hydrogen for a time sufficient for catalyst activation at a temperature sufficient for catalyst activation, but below 250° C. and at a pressure sufficient for catalyst activation above 1000 psig.

The flow of hydrogen will generally be in the range of about 0.1 to about 10 liters per minute per 50 milliliters of catalyst and the time of contact will be in the range of about 8 to about 36 hours. In a preferred embodiment of the invention the flow of hydrogen is in the range of about 0.25 to about 6 liters per minute per 50 milliliters of catalyst, the time of contact is from about 12 to about 30 hours, the activation temperature is within a range of about 50° to about 250° C., and the activation pressure is in a range of 1000 to about 5000 psig (6.9 to about 34.5 MPa). The most preferred range for the activation temperature is from about 100° to about 200° C. and for the activation pressure is from about 1300 to about 3000 psig (9.0 to 20.7 MPa).

In another embodiment of this invention chemical compounds containing at least one nitrile group, i.e., nitriles and dinitriles etc., are hydrogenated by contacting the compounds with hydrogen under hydrogenation conditions in the presence of a cobalt hydrogenation catalyst that has been activated by the method described above.

The instant invention is broadly concerned with the more efficient utilization of cobalt catalysts in the hydrogenation of nitriles and dinitriles to amines and diamines. Said nitriles and dinitriles can be termed the hydrogenation substrate in the instant invention. Broadly the hydrogenation substrates of the instant invention contain from 2 to 30 carbon atoms per molecule, preferably from 4 to 20 carbon atoms per molecule. The substrates according to the instant invention contain at least one nitrile group and may also contain other groups such as hydroxyl, amine, ester, carboxylic acid, aryl, and ether.

Examples of suitable hydrogenation substrates include acetonitrile, hydroxypropionitrile, benzonitrile, cyanoacetic acid, ethyl cyanoacetate, 3-methoxypropionitrile, adiponitrile, 5-aminocapronitrile, 5-methylnonanedinitrile, 2,4-dimethyloctanedinitrile, 2,4,6-trimethylheptanedinitrile, and the like.

A preferred hydrogenation substrate for the practice of this invention is a mixture of 5-methylnonanedinitrile, 2,4-dimethyloctanedinitrile, and 2,4,6-trimethylheptanedinitrile.

The hydrogenation catalysts which are utilized in the instant invention are those based on cobalt. For example, the catalyst can be elemental cobalt or compounds of cobalt which are reducible by hydrogen to finely divided elemental cobalt. Suitable hydrogen reducible compounds include the oxides, halides, nitrates, oxalates, acetates, carbamates, propionates, tartrates, hydroxides, and the like and mixtures thereof. Specific examples include elemental cobalt, cobalt oxide, cobalt chloride, cobalt nitrate, cobalt acetate, cobalt carbonate, cobalt hydroxide, and the like.

In the practice of this invention it is preferable to employ unsupported cobalt catalysts. These unsupported cobalt catalysts will generally be a mixture of cobalt and cobalt oxide in such proportions that the catalyst will contain about 70 to 95, preferably about 75 to 90 weight percent cobalt. An example of a suitable unsupported catalyst is a commercial cobalt catalyst, Harshaw Co. 1606, which contains 80.5 weight percent cobalt, 11.4 weight percent oxygen, 4.2 weight percent carbon, 0.45 weight percent calcium, 0.1 weight percent copper, 0.14 weight percent nickel, and 0.07 weight percent iron.

In the practice of this invention, it is also possible to employ catalytic amounts of elemental cobalt on a solid catalyst carrier which does not deleteriously affect the catalytic hydrogenation process of this invention. Such supports include, for example, carbon, kieselguhr, silica, alumina, silica-alumina, calcium carbonate, asbestos, pumice, clays, and the like and mixtures thereof. The cobalt can be added to the catalyst support by any of the methods well known in the art. For example, the supported catalyst can be prepared by dry mixing the components or by impregnating the support with a solution or dispersion of cobalt in elemental form or in the form of reducible compounds thereof. The supported catalysts can be pretreated with hydrogen to reduce the cobalt compounds, or such reduction can be achieved in the hydrogenation reactor. When a support is employed, the amount of cobalt on the support material will generally be in the range of about 5 to 80, preferably 15 to 65 weight percent based on the weight of the total catalyst components. An example of a suitable supported catalyst includes 16% cobalt on alumina based on the total weight of catalyst and support material.

The amount of catalyst employed in the hydrogenation process of the instant invention for a batch process can be expressed in terms of the weight percent of catalytic metal based on the weight of compound being hydrogenated. The amount of catalyst will be in the range of broadly 0.1 up to 20 and preferably from 0.5 up to 5 weight percent cobalt based on the weight of hydrogenation substrate. For a continuous process, the amount of catalyst will be such that a liquid hourly space velocity (LHSV) of broadly 0.1 to 10 and preferably 0.5 to 5 volumes of substrate plus diluent per volume of catalyst will be attained.

The hydrogen pressure utilized in the hydrogenation according to the instant invention is broadly from about 500 to about 5000 psig (3.5 to 34.5 MPa), and preferably about 1000 to about 3000 psig (6.9 to 20.7 MPa). The temperatures utilized in the hydrogenation process of the instant invention are broadly from about 25° to about 250° C. and preferably about 50° to about 150° C. The time employed in the hydrogenation process of the instant invention is not particularly critical and will generally range from a few minutes to about 5 hours for a batch process.

Ammonia is the preferred diluent for the hydrogenation of the instant invention and also acts to suppress side reactions such as secondary and tertiary amine formation. Other suitable diluents are primary, secondary, and tertiary alkyl amines, such as methylamine, dimethylamine, diethylamine, and trimethyl amine. The diluent is present in a mole ratio of diluent to nitrile group (two nitrile groups per molecule of dinitrile as used in the examples that follow) of broadly 1:1 to about 100:1, preferably 5:1 to 50:1.

Water, tertiary alcohols, and aliphatic hydrocarbons will not normally be present during the hydrogenation and may, in some cases, be detrimental to the hydrogenation. In those cases where the presence of water, tertiary alcohols, aliphatic hydrocarbons, or mixtures thereof are shown to be either non-detrimental or beneficial to the hydrogenation, they may be present in amounts up to about 30 weight percent of the diluent used.

EXAMPLES

In all of the examples that follow, the nitrile substrate which is undergoing hydrogenation is an unsaturated dinitrile mixture obtained by the reaction of isobutylene and acrylonitrile. This unsaturated dinitrile mixture comprises 5-methyl-4-nonenedinitrile, 2,4-dimethyl-4-octenedinitrile, 2,4-dimethyl-3-octenedinitrile, 2,4,6-trimethyl-3-heptenedinitrile, 5-methylenenonanedinitrile, 2-methyl-4-methyleneoctanedinitrile, and 2,6-dimethyl-4-methyleneheptanedinitrile. For convenience, the above mixture will be described as diadduct in the examples presented below.

The hydrogenation of the instant invention is intended for the hydrogenation of nitrile groups. The diadduct, an unsaturated dinitrile, was used as the hydrogenation substrate due to its availability. The olefinic unsaturation was incompletely hydrogenated and was not considered in product analysis.

The catalyst used in all of the following examples was a commercial catalyst—Harshaw Co. 1606—which is made by Harshaw Chemical Company and has the following composition:

| | Weight Percent |
|---|---|
| cobalt | 80.5 |
| oxygen | 11.4 |
| carbon | 4.2 |
| calcium | 0.45 |
| copper | 0.1 |
| nickel | 0.14 |

-continued

| | Weight Percent |
|---|---|
| iron | 0.07 |

Co 1606 has a surface area of 16 m$^2$/g and a pore volume, below 600 Å in diameter, of 0.12 ml/g.

EXAMPLE I

A test was devised to allow a wide range of catalyst activation conditions to be tested without requiring extended hydrogenation runs to be held at all conditions. A 20″ (508 mm) long by ½″ (12.7 mm) diameter tubular reactor fitted with a heating system and temperature recorder was filled in order with 30 g (30 ml) of an inert α-alumina bed support, 20 g (8.33 ml) of the cobalt catalyst (previously activated), and 20 g (20 ml) of an inert α-alumina. The cobalt catalyst activation conditions included a variety of temperatures, pressures, and times. The reactor was flushed with nitrogen, preheated at 100° C. and 1500 psig (10.4 MPa) with a hydrogen flow of one liter per minute for one hour, and then a mixture of diadduct and ammonia (in a weight ratio of 1:9) was fed to the reactor at a liquid hourly space velocity (LHSV) of about 6. Reactor conditions were 100° C., 1500 psig (10.4 MPa), and one liter per minute hydrogen flow. Samples of the hydrogenation product were taken at the end of one and two hours of operation and analyzed for amine and nitrile content by gas-liquid chromatography after removing the ammonia diluent. The results of the runs are presented in Table I, in terms of the amine/nitrile ratio along with the activation conditions used in each run.

TABLE I

| | Activation Conditions[a] | | | Product Analysis[b] (amine/nitrile) | |
|---|---|---|---|---|---|
| Run No. | Temp. (° C) | Pressure (psig)(MPa)[c] | Time (Hr) | One Hour | Two Hours |
| 1 | 150 | 14.7(0.1) | 2 | 3/1 | 3/1 |
| 2 | 250 | 14.7(0.1) | 2 | 2/1 | 2/1 |
| 3 | 350 | 14.7(0.1) | 2 | 2/1 | 2/1 |
| 4 | 450 | 14.7(0.1) | 2 | 1/1 | 1/2 |
| 5 | 150 | 1000(6.9) | 2 | 8/1 | 8/1 |
| 6 | 150 | 1500(10.4) | 2 | 9/1 | 9/1 |
| 7 | 150 | 1500(10.4) | 8 | 19/1 | 19/1 |
| 8 | 150 | 1500(10.4) | 24 | 100/0 | 100/0 |

[a]Conditions used for the catalyst activation before the hydrogenation run. Hydrogen flow rate is 6 liters per minute per 50 milliliters of catalyst.
[b]Analysis of hydrogenation product at the indicated number of hours in the run in terms of a ratio of amine groups to nitrile groups. A higher ratio indicates that more nitrile hydrogenation has occurred.
[c]MPa is mega Pascal.

The results of these runs indicate that a lower activation temperature (note increasing temperature in runs 1, 2, 3, and 4), a higher activation pressure (note increasing pressure in runs 1, 5, and 6), and a longer activation time (note lengthening activation times in runs 6, 7, and 8) give more complete nitrile hydrogenation. Run #8, which used activation conditions of 150° C. and 1500 psig (10.4 MPa), for 24 hours, gave complete hydrogenation.

EXAMPLE II

A series of runs was made using a ½″ (12.7 mm) diameter × 20″ (508 mm) length laboratory continuous reactor. The catalyst was charged to the reactor and reduced with hydrogen using conditions of temperature, pressure, and time as described in Table II. The reactor temperature and hydrogen pressure were adjusted to the values desired for the hydrogenation — 100° C., 1500 psig (10.4 MPa), and a hydrogen flow rate of 1 liter per minute unless otherwise noted — and a mixture of diadduct and ammonia in a 1:9 weight ratio was fed continuously with hydrogen to the reactor. The hydrogenation product was analyzed by gas-liquid chromatography after the diluent was removed by distillation at atmospheric pressure. The amount of heavies present in the hydrogenation product during the run was determined by distilling the product and weighing the pot residue. Table II presents the results of the hydrogenations.

Runs 9 through 13 show that with activation of the Co 1606 catalyst at 150° to 170° C. and 1500 psig (10.4 MPa) for 18 to 24 hours, hydrogenation of diadduct occurred with no nitrile being detected in the product for reaction times of 168 hours (run 10) to 406 hours (run 9) at a LHSV = 1. Runs 11 and 12 had a different catalyst bed arrangement (the top half of the bed was a 50:50 mixture of Co 1606 and an inert alumina) and showed catalyst bed collapse and plugging in the top half. Run 13, using higher pressure and lower temperatures, operated 476 hours (LHSV = 2) with no nitrile present in the product and no change in the catalyst.

(9/2 weight ratio) as diluent and Co 1606 as catalyst. The activation conditions (with a hydrogen flow of 0.833 liters per minute per 50 milliliters of catalyst) and hydrogenation results are shown in Table III. In contrast with runs 9 to 13 with ammonia as the sole diluent, all runs with t-butyl alcohol/ammonia as diluent had nitrile in the product after relatively short times. Run 21, which used activation conditions that were optimum for runs using only ammonia as a diluent (150° C. and 1500 psi for 24 hours), was not significantly better than run 16, which had a shorter activation time (2 hours). Although different pressures were used in these two hydrogenations (2500 psig in run 16 and 1500 psig in run 21), considering the higher level of nitrile in the product of run 21, the results of runs 16 and 21 are similar. Run 17, which used high temperature, low pressure, and short time for activation, had 5% nitrile content after 118 hours (at LHSV = 2). Runs 18, 19, and 20 had nitrile groups present in the product after short periods of time, but the activation pressure was not recorded. The results of these runs using a 9/2 weight ratio of t-butyl alcohol and ammonia suggests that there is particular sensitivity of Co 1606, cobalt catalyst to activa-

TABLE II

| | Activation Conditions[a] | | | | Hydrogenation Results | | | |
|---|---|---|---|---|---|---|---|---|
| Run No. | Temp., °C | Pressure, psig (MPa) | Time, hours | Rate[e] | Reaction Stopped, Hours | Nitrile Content, % | Heavies, % | Catalyst Condition |
| 9 | 150 | 1500(10.4) | 24 | 1 | 406 | 0 | 2.1, 4.6 | ND |
| 10 | 170 | 1500(10.4) | 24 | 1 | 168 | 0 | ND[f] | Small amount of physical decomposition |
| 11[c] | 170 | 1500(10.4) | 18 | 1 | 216 | 0 | ND | A small section collapsed |
| | | | | 2 | 165 | | | |
| 12[c] | 170 | 1500(10.4) | 18 | 1 | 92 | 0 | ND | Plugged |
| | | | | 2 | 312 | | | |
| 13[d] | 150–160 | (b) | 24 | 2 | 476 | 0 | 0.47, 0.76 | OK |
| 14 | 350 | 1500(10.4) | 24 | 1 | 48 | 5 | ND | OK |
| 15 | 150 | 1500(10.4) | 2 | 1 | 144 | 10 | ND | OK |

[a]Conditions used to activate catalyst before the hydrogenation reaction. Hydrogen flow rate is 0.833 liters per minute per 50 milliliters of catalyst.
[b]Pressure not recorded. The inventor believes that the pressure was 1500 psig.
[c]Catalyst bed consisted of two parts; top half is 50:50 Co 1606: an inert α-alumina and bottom half is Co 1606 only.
[d]Hydrogenation conditions were 2500 psig (17.2 MPa) and 75° C. Diadduct had been passed over alumina before hydrogenation.
[e]Liquid Hourly Space Velocity (LHSV).
[f]ND = Not Determined.

In run 14, in which a higher activation temperature was used, nitrile groups appeared in the hydrogenation product after only 48 hours. In run 15, in which a shorter activation time was used, nitrile groups appeared in the hydrogenation product after only 144 hours. As found in the runs of Example 1, the use of higher activation temperatures and shorter activation times than disclosed in the instant invention resulted in inferior hydrogenation results.

tion conditions with ammonia alone as a diluent.

I claim:

1. A method for activating a cobalt hydrogenation catalyst consisting essentially of contacting a flow of hydrogen with elemental cobalt or compounds of cobalt chosen from among oxides, halides, nitrates, oxalates, acetates, carbamates, carbonates, priopionates, tartrates, and hydroxides, which are reducible by hydrogen to finely divided elemental cobalt for a time

TABLE III

| | Activation Conditions | | | | Hydrogenation Results[a] | | |
|---|---|---|---|---|---|---|---|
| Run No. | Temperature, °C | Pressure, psig (MPa) | Time, Hours | LHSV | Reaction Stopped, Hours | Nitrile Content, % | Catalyst Condition |
| 16 | 150° C | 1500(10.4) | 2 | 1 | 140[d] | 2 | Slight decomposition |
| 17[c] | 350 | 14.7 (0.1) | 2 | 2 | 118 | 5 | ND |
| 18 | 350–375 | (b) | 2 | 2 | 22 | 5 | ND |
| 19 | 375 | (b) | 2½ | 2 | 4½ | 5 | ND |
| 20 | 375 | (b) | 2½ | 2 | 5 | 20 | ND |
| 21[e] | 150 | 1500(10.4) | 24 | 1 | 152 | 10 | Slight decomposition |

[a]Hydrogenation of diadduct (DA) over Co 1606 using a weight ratio of DA/t-butyl alcohol/NH₃ of 1/9/2 at 2500 psi (17.2 MPa) and 100° C unless otherwise noted.
[b]Not recorded in notebook.
[c]Hydrogenation temperature = 80° C.
[d]Heavies level = 4.4% at 68 hours, 2.2% at 140 hours.
[e]Hydrogenation pressure = 1500 psig.

EXAMPLE III

A series of runs was made with the same apparatus as in Example II and with t-butyl alcohol and ammonia sufficient for catalyst activation at a temperature sufficient for activation in a range of about 100°–200° C. and at a pressure sufficient for activation above 1000 psig.

2. A method of claim 1 wherein the flow of hydrogen is in the range of about 0.1 to about 10 liters per minute per 50 milliliters of catalyst and the time is in the range of about 8 to about 36 hours.

3. A method of claim 1 wherein the pressure is in the range of about 1300 to about 3000 psig.

4. A method of claim 3 wherein the pressure is in the range of about 3000 psig.

5. A method of claim 1 wherein the catalyst is unsupported.

6. A method of claim 1 wherein the catalyst is supported on a solid catalyst carrier.

7. A method of hydrogenating nitriles and dinitriles to amines and diamines comprising contacting a chemical compound containing at least one nitrile group with hydrogen under hydrogenation conditions in the presence of a cobalt hydrogenation catalyst activated by the method of claim 1.

8. A method of claim 7 wherein the hydrogenation is in the presence of a diluent.

9. A method of claim 8 wherein the diluent is ammonia.

10. A method of claim 7 wherein the hydrogenation is carried out at a pressure in the range of about 500 to about 5000 psig and a temperature in the range of about 25° to about 250° C.

* * * * *